United States Patent
Gumbrecht et al.

(10) Patent No.: US 7,572,624 B2
(45) Date of Patent: Aug. 11, 2009

(54) DNA CHIP COMPRISING A MICROARRAY MADE OF AN MICROELECTRODE SYSTEM

(75) Inventors: Walter Gumbrecht, Herzogenaurach (DE); Konrad Mund, Uttenreuth (DE); Meinrad Schienle, Neubiberg (DE); Roland Thewes, Gröbenzell (DE)

(73) Assignee: Siemens Aktiengesellschaft, Munich (DE)

( * ) Notice: Subject to any disclaimer, the term of this patent is extended or adjusted under 35 U.S.C. 154(b) by 10 days.

(21) Appl. No.: 10/539,817

(22) PCT Filed: Dec. 15, 2003

(86) PCT No.: PCT/DE03/04127

§ 371 (c)(1),
(2), (4) Date: Mar. 27, 2006

(87) PCT Pub. No.: WO2004/057334

PCT Pub. Date: Jul. 8, 2004

(65) Prior Publication Data

US 2006/0216813 A1 Sep. 28, 2006

(30) Foreign Application Priority Data

Dec. 19, 2002 (DE) ................. 102 59 820

(51) Int. Cl.
*C12M 1/34* (2006.01)
*C12M 3/00* (2006.01)

(52) U.S. Cl. ................................. 435/287.2
(58) Field of Classification Search ............... 435/287.2
See application file for complete search history.

(56) References Cited

U.S. PATENT DOCUMENTS

| | | | | |
|---|---|---|---|---|
| 5,567,301 A | * | 10/1996 | Stetter et al. | 205/777.5 |
| 5,704,975 A | | 1/1998 | Kobayashi et al. | |
| 6,169,394 B1 | * | 1/2001 | Frazier et al. | 324/71.4 |
| 6,485,703 B1 | * | 11/2002 | Cote et al. | 424/9.1 |
| 7,087,148 B1 | * | 8/2006 | Blackburn et al. | 205/452 |
| 7,208,077 B1 | * | 4/2007 | Albers et al. | 205/782 |

(Continued)

FOREIGN PATENT DOCUMENTS

DE  19610115  9/1997

(Continued)

OTHER PUBLICATIONS

Japanese Office Action mailed on Aug. 7, 2008 for corresponding Japanese Patent Application No. 2004-561039.

(Continued)

*Primary Examiner*—Walter D Griffin
*Assistant Examiner*—Lydia Edwards
(74) *Attorney, Agent, or Firm*—Harness, Dickey & Pierce, P.L.C.

(57) ABSTRACT

A DNA chip includes a carrier and a microarray of spots containing immobilised catcher molecules which are arranged on the carrier. Each spot contains a microelectrode system for the impedance spectroscopic detection of binding events occurring between the catcher molecules and target molecules of an analyte solution applied to the spots. The microelectrode system has a pair of polarisation electrodes in order to produce an alternating electromagnetic field and a pair of sensor electrodes for measuring a voltage drop in the analyte.

18 Claims, 7 Drawing Sheets

U.S. PATENT DOCUMENTS

| | | |
|---|---|---|
| 2002/0015993 A1 | 2/2002 | John et al. |
| 2002/0028441 A1 | 3/2002 | Hintsche et al. |
| 2002/0172969 A1* | 11/2002 | Burns et al. ............... 435/6 |
| 2003/0070942 A1 | 4/2003 | Ossart |
| 2004/0063152 A1 | 4/2004 | Gumbrecht et al. |
| 2004/0197899 A1* | 10/2004 | Gomez et al. ............ 435/287.2 |

FOREIGN PATENT DOCUMENTS

| | | |
|---|---|---|
| DE | 10015816 | 10/2001 |
| JP | 55138397 | 10/1980 |
| JP | 2504069 | 11/1990 |
| JP | 7508831 | 9/1995 |
| JP | 2590728 | 12/1998 |
| WO | WO 9012314 | 10/1990 |
| WO | WO 98/19153 | 5/1998 |
| WO | WO 00/62047 | 10/2000 |
| WO | WO 00/63682 | 10/2000 |
| WO | WO/0062048 * | 10/2000 |
| WO | WO 01/44805 | 6/2001 |
| WO | WO 01/79828 | 10/2001 |
| WO | WO/0183674 * | 11/2001 |
| WO | WO 0242759 A1 | 5/2002 |

OTHER PUBLICATIONS

M. Paeschke et al.: Voltammetric Multichannel Measurements Using Silicon Fabricated Microelectrode Arrays, Electroanalysis 8, No. 10, S. 891-899, 1996.

R. Hintsche et al.: Microbiosensors Using electrodes Made in Si-Technology, Frontiers in Biosensorics, Fundamental Aspects, edited by F.W. Scheller et al., Dirk Hauser Verlag, Basel, S. 267-283, 1997.

German Translation Aid. Date Unknown.

German Office Action Dated Mar. 24, 2005.

International Search Reports (English and German) dated May 5, 2004.

* cited by examiner $l \gg w$
$g = w$ a)

b)

a)

b)

a)

b)

c)

d)

400
DNA CHIP COMPRISING A MICROARRAY MADE OF AN MICROELECTRODE SYSTEM

This application is a PCT National Stage Application of PCT/DE2003/004127 filed Dec. 15, 2003, which claims priority under on German Patent Application No. DE 102 598 20.7 filed in Germany on Dec. 19, 2002, the entire contents of which is hereby incorporated herein by reference.

FIELD

The invention generally relates to a DNA chip comprising a microarray made of microelectrode systems.

BACKGROUND

A DNA chip generally includes a carrier usually of planar design, on which a microarray of spots is arranged. A spot contains catcher molecules, for example oligonucleotides, immobilized on the surfaces of carrier and electrodes.

In order to carry out an analysis, an analyte solution containing target molecules, for example DNA fragments, is applied to the spots. In the case of a complementary matching in the base sequence, the target molecules couple to the catcher molecules of a spot. The reading-out of the analysis result, that is to say the determination of those spots in which coupling or binding events have taken place, may be effected optically, calorimetrically or electrically, by way of example.

DE 196 10 115 C2 and the publication "Nanoscaled interdigitated electrode arrays for biochemical sensors", Van Gerwen et al., Sensors and Actuators, B49, 1998, 73-80, Elsevier Science S. A., disclose electrically readable DNA chips having two-pole microelectrode systems for the electrical detection of binding events. These systems are each formed from a pair of comblike, intermeshed electrodes to which AC current is applied. Binding events that take place in the region of the electrodes alter electrical parameters such as e.g. the conductance and the specific capacitance of the analyte and can accordingly be detected with the aid of the microelectrode system.

What is problematic in the case of DNA chips of this type is that the dimensioning of the electrodes is very large in comparison with the molecular dimensions of the catcher molecules present in a monomolecular layer on the carrier and electrode surface. Binding events that take place there can therefore be detected only with difficulty. Van Gerwen et al. propose miniaturizing the electrodes in order to improve the measuring effect or the sensitivity. However, limits are imposed on miniaturization for technical and economic reasons.

A further problem resides in the fact that relatively high electrolyte conductances and accordingly low analyte resistances are present during the detection of biochemical molecules. They have superposed on them the usually very high electrode impedance brought about by the electrolyte double layer capacitance between electrodes and analyte. It is virtually impossible to separate analyte resistance and electrode impedance. Moreover, very high measurement frequencies are necessary on account of the small analyte resistance. This is very difficult with conventional measurement technology, however, since parasitic capacitances such as cable capacitances, etc. disturb the measurement.

In the case of conventional DNA chips, therefore, the measuring effects for determining the capacitance or the resistance of the analyte are very weakly pronounced or absent. What is more, the measurement frequencies have to lie in the MHz range. Moreover, all chemical or physical processes that take place at the electrodes influence the measurement between the electrodes, thus e.g. coatings with biochemical molecules, polarizations, corrosion of the electrodes, film formation, etc.

Furthermore, DE 100 15 816 A1 discloses an electrically readable DNA chip which enables a two-pole electrode system for the electrical monitoring of a redox cycling process. If appropriate, in this respect there may furthermore be a third electrode with potential application for the control of the redox cycling process.

SUMMARY

It is an object of an embodiment of the invention to provide an improved electrically readable DNA chip which facilitates the detection of analyte-specific measured values.

In the case of an embodiment of the invention, the microelectrode system may be constructed as a thin-film four-pole system. In this case, the DNA chip includes a pair of polarization electrodes for generating an alternating electromagnetic field and a pair of sensor electrodes for measuring a binding-induced voltage drop in the analyte.

In this case, AC current or voltage having a given amplitude and a given frequency is applied to the polarization electrodes. With the aid of the sensor electrodes and a high-resistance measuring amplifier connected thereto, a change in resistance caused by binding events can be tapped off as a change in voltage in a manner free of polarization. The disturbing influence of the electrode impedance is thus eliminated.

The voltage is tapped off at the sensor electrodes in high-resistance fashion, so that no appreciable currents exit from or enter into the sensor electrodes. Moreover, as a result of this, no additional polarization takes place at the sensor electrodes, which minimizes the above-described disadvantageous effects such as polarization, film formation, oxidation, etc.

Although these effects may still occur at the polarization electrodes, they do not influence the measurement results, or have only a substantially smaller influence on the measurement results. This occurs owing to the voltage measurement being purely by way of the sensor electrodes.

By virtue of the separation of polarizing polarization electrodes and measuring sensor electrodes, at which practically no disturbing chemical or physical processes take place, the quality of the measurement is advantageously considerably increased. The construction of the four-pole system with thin-film electrodes is essential in this embodiment, it advantageously being possible for such thin-film electrodes to be integrated into the chip by way of the methods known in semiconductor technology.

In one preferred refinement of an embodiment of the invention, the carrier of the DNA chip has a silicon substrate, on which the microelectrode system is integrated preferably using thin-film technology. In this case, the electrodes are directly connected to an integrated circuit situated in the Si substrate. What is advantageous in this case is, in particular, the absence of lead capacitances, which would become apparent in disturbing fashion primarily during measurements in the relatively high frequency range, e.g. starting from 10 MHz. Consequently, a DNA chip of the refinement mentioned can also be employed at high measurement frequencies.

Despite the measures described, there are still further parasitic capacitances present between the electrodes involved in the measurement, which, in unfavorable cases, may interfere with the impedance measurement in the analyte. In order to remedy this, in a further preferred refinement of an embodiment of the invention, a sensor electrode is assigned a shielding electrode, which is held at the same electrical potential as the sensor electrode.

Preferably, the electrical potential of the sensor electrode is held at the shielding electrode by a buffer amplifier connected to the sensor electrode and having a gain of 1. The buffer amplifier as an active electronic element decouples potential and current intensity, or charge. The parasitic capacitances occurring between the additional shielding electrodes and the other electrodes are thus electrically ineffective for the measurement since the charging or discharging of the capacitances is performed by the active amplifier, thus relieving the loading on the measuring apparatus and the sensor electrodes for the potential measurement.

Shielding electrodes may be embodied for example, on both sides of the sensor electrodes or lie only between sensor electrodes and polarization electrodes. The effects of shielding by the shielding electrodes and the increasing distance of an electrode unit through insertion of shielding electrodes are to be weighed up relative to one another in the individual case.

The buffer amplifier is integrated on the DNA chip. This results in a particularly compact and effective construction of the DNA chip. The leads are kept as short as possible and disturbances are thus precluded as well as possible in all of the signal lines.

In order to avoid a current flow that corrupts the measurement within the sensor electrodes and also the shielding electrodes, these electrodes should be significantly smaller than the potential electrodes. Given a width of the potential electrodes of 1 µm, this would mean further miniaturization that could no longer be realized technically for the electrodes mentioned.

A different path is taken, therefore, in one preferred embodiment. In this case, sensor and/or shielding electrodes are completely directly electrically isolated from the analyte, thereby preventing a current flow between analyte and electrodes.

In another preferred exemplary embodiment, this is achieved by way of a pointlike configuration of the sensor electrodes. In this case, it is necessary for a device for tapping off the voltage drop at the sensor electrodes to have a high input resistance and a low input capacitance. The electrical connection of the pointlike sensor electrodes is preferably realized by way of a collective line that is embedded ("buried") in the substrate and is electrically connected to the sensor electrodes via plated-through holes.

In order to ensure the suitability of a DNA chip as a biochemical analysis system, the electrode geometries and thus the impedance-spectroscopic detection range have to be approximated as far as possible to the dimensions of biochemical molecules. However, miniaturization that falls below electrode widths of approximately 500 nm can be realized only with extremely complicated technology at very high cost.

An aggravating factor here in the case of a 4-electrode system is that the distance between the polarization electrodes is intrinsically greater than in the case of a 2-electrode system since, after all, further electrodes, e.g. the sensor electrodes, lie between the polarization electrodes. In a particular preferred embodiment variant, then, a reaction layer embedding the microelectrode system is provided, which substantially enlarges the space in which binding events take place and can be detected in an impedance-spectroscopic fashion. Consequently, the reaction layer makes it possible to considerably increase the number of detectable binding events and thus the measuring effect or the sensitivity of a DNA chip.

The reaction layer preferably has a thickness that is correlated with the width of the electrodes, and advantageously corresponds to approximately 5-10 times the electrode width. In any event, the reaction layer should have a thickness of less than 100 µm since otherwise the result would be excessively long diffusion paths and, associated therewith, excessively long reaction times for transporting the target molecules to the catcher molecules. If the electrode width is assumed to be 1 µm (1000 nm), the thickness of the reaction layer is approximately 5 to 10 µm. This ensures that the target molecules contained in an analyte solution applied to the reaction layer can indiffuse at sufficient speed. Hydrogels have been found to be particularly suitable for the construction of a reaction layer.

BRIEF DESCRIPTION OF THE DRAWINGS

Further details and advantages of the invention emerge from the following description of figures of example embodiments with reference to the drawings. In the figures.

DETAILED DESCRIPTION OF THE EXAMPLE EMBODIMENTS

Figure 1:
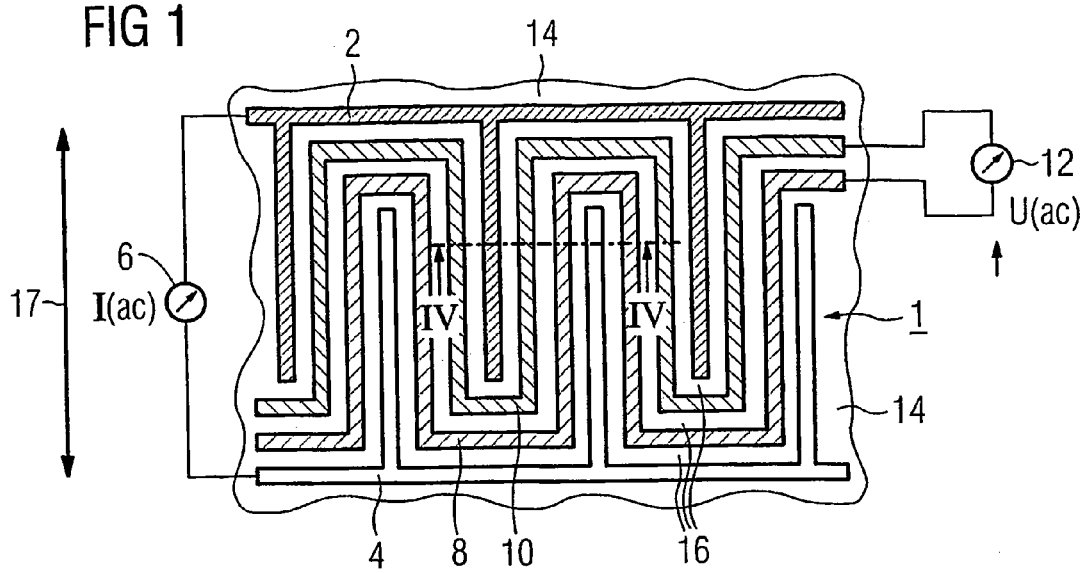
FIG. 1 shows the plan view of a DNA chip with an electrode microsystem in an interdigital structure.

FIG. 1 shows a detail from a DNA chip in plan view, a carrier 14 being indicated. The detail shows a spot 1. The microelectrode system thereof exhibits a pair of polarization electrodes 2 and 4. The polarization electrodes 2 and 4 are fed by a current source 6. The current source 6 generates an AC current that flows through the electrodes 2 and 4 and polarizes an analyte (not specifically illustrated) situated above the electrode arrangement. The analyte thus closes the electric circuit via current source 6 and polarization electrodes 2 and 4.

Furthermore, FIG. 1 illustrates a pair of sensor electrodes 8 and 10, which are connected to a high-resistant voltmeter 12. Since current lines form between the two polarization electrodes 2 and 4 in an electrically conductive analyte applied to the carrier 14 and the electrodes, the sensor electrodes 8 and 10 are in contact with regions of the analyte at a different electrical potential. This potential difference is then indicated at the voltmeter 12. Since the voltmeter 12 has a high input resistance, however, no appreciable charge transport, that is to say no appreciable current flow, takes place between the analyte and the sensor electrodes 8 and 10.

All four electrodes 2, 4, 8 and 10 in FIG. 1 are arranged in an interdigital structure in FIG. 1. The electrode arrangement illustrated is applied as part of a microchip by using thin-film technology, by way of example, on a carrier 14, for example silicon with an electrically insulating covering layer (not illustrated), e.g. silicon oxide. All the electrodes are isolated from one another by electrically insulating interspaces 16. The symbolically represented current source 6 and the voltmeter 12 are generally embodied as integrated electrical circuits in the carrier 14 e.g. beneath the electrodes. The arrangement is illustrated in a manner highly compressed in direction of extent 17. The same applies to FIGS. 2, 3 and 6.

Figure 2:
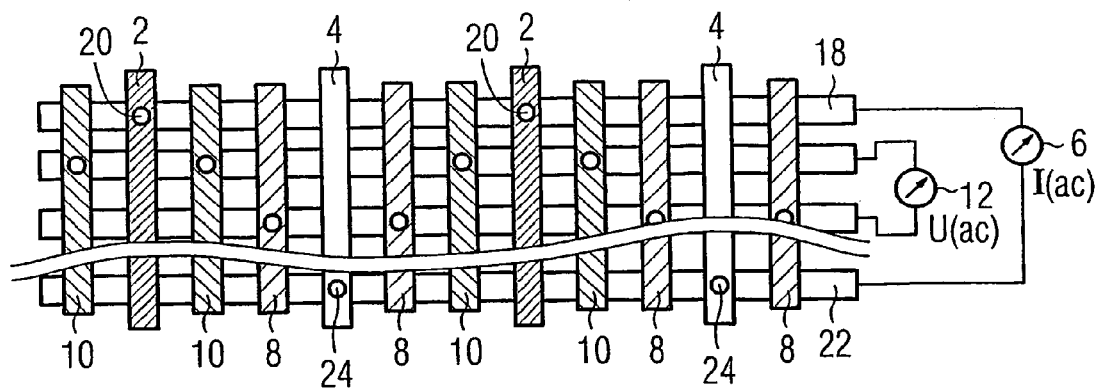
FIG. 2 shows the plan view of an electrode microsystem with buried collective lines.

The embodiment of the invention illustrated in FIG. 2 likewise includes a pair of polarization electrodes 2 and 4 and a pair of sensor electrodes 8 and 10. However, the individual sections of the electrodes are not folded into one another in comblike or meandering fashion as in FIG. 1. Each type of electrode is embodied in each case as a plurality of elongate strips that are inherently electrically insulated from one another on the chip surface. Thus, two strips each of the polarization electrodes 2 and 4 and four strips each of the sensor electrodes 8 and 10 can be seen.

For electrical connection, in this case each type of electrode is assigned an electrode collective line. The polarization electrode 2 is assigned the collective line 18, by way of example. The two strips of the polarization electrode 2 are therefore connected to the collective line 18 assigned to it with the aid of electrical plated-through holes 20. The collective line 18 is electrically insulated from all the other electrodes 4, 8 and 10.

Therefore, collective lines lie for example buried in the insulating covering layer 36 of the carrier 14 or are at least electrically insulated in some other way both relative to one another and from all the electrodes. The second polarization electrode 4 is assigned the collective line 22 with corresponding plated-through holes 24, etc.

Figure 3:
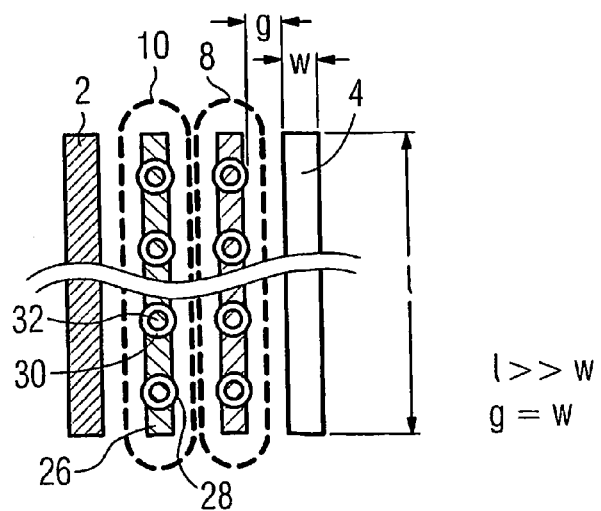
FIG. 3 shows the plan view of an electrode microsystem with pointlike sensor electrodes.

It can be seen in FIG. 3, and also from FIGS. 1 and 2, that the geometrical dimensions of width w and spacing g of the polarization and sensor electrodes are approximately identical in magnitude. This may possibly lead to problems since, in the case of a four-pole measuring method, the sensor electrodes are usually all made substantially smaller than the polarization electrodes.

Therefore, an alternative embodiment of sensor electrodes is illustrated in FIG. 3. The sensor electrode 10 contains a collective line 26, which, in accordance with the collective lines 18 and 22 in FIG. 2, is embodied such that it is buried in the substrate or is sufficiently electrically insulated from e.g. other lines and the analyte. The contact between the sensor electrode 10 and the analyte is no longer produced areally as in FIGS. 1 and 2, but rather only by way of pointlike individual electrodes 28.

Each individual electrode 28 contains a pointlike electrode head 30 that is connected to the electrode collective line 26 with the aid of an electrical plated-through hole 32. Although the electrode width w and the electrode spacing g are identical, this measure indicates that the effective electrode area of the sensor electrodes 8 and 10 is substantially smaller in comparison with the area of the polarization electrodes 2 and 4. It is indicated once again here that in real arrangements the "length" l of the electrode is substantially greater than the width w thereof.

Figure 4:
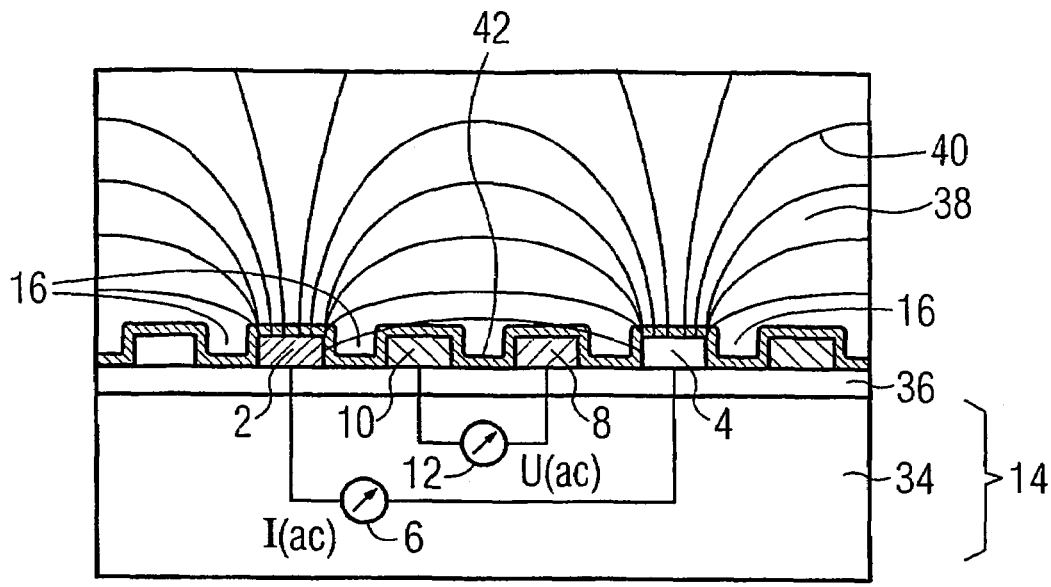
FIG. 4 shows the section through the electrode microsystem from FIG. 1 along the line IV-IV without (a) and with (b) a reaction layer.
Figure 4:
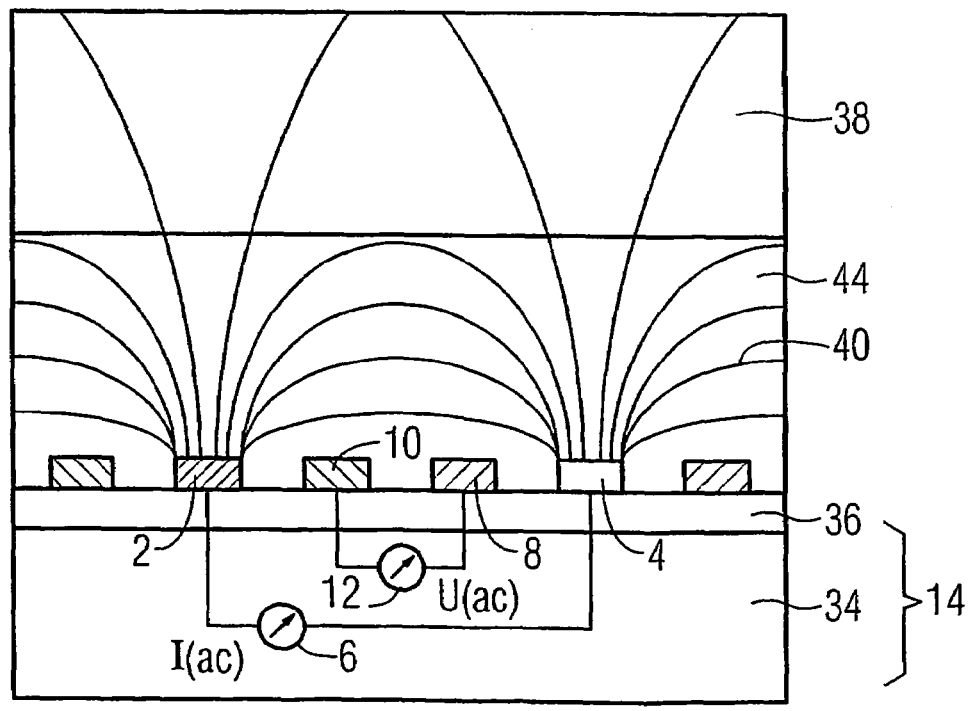
Figure 5:
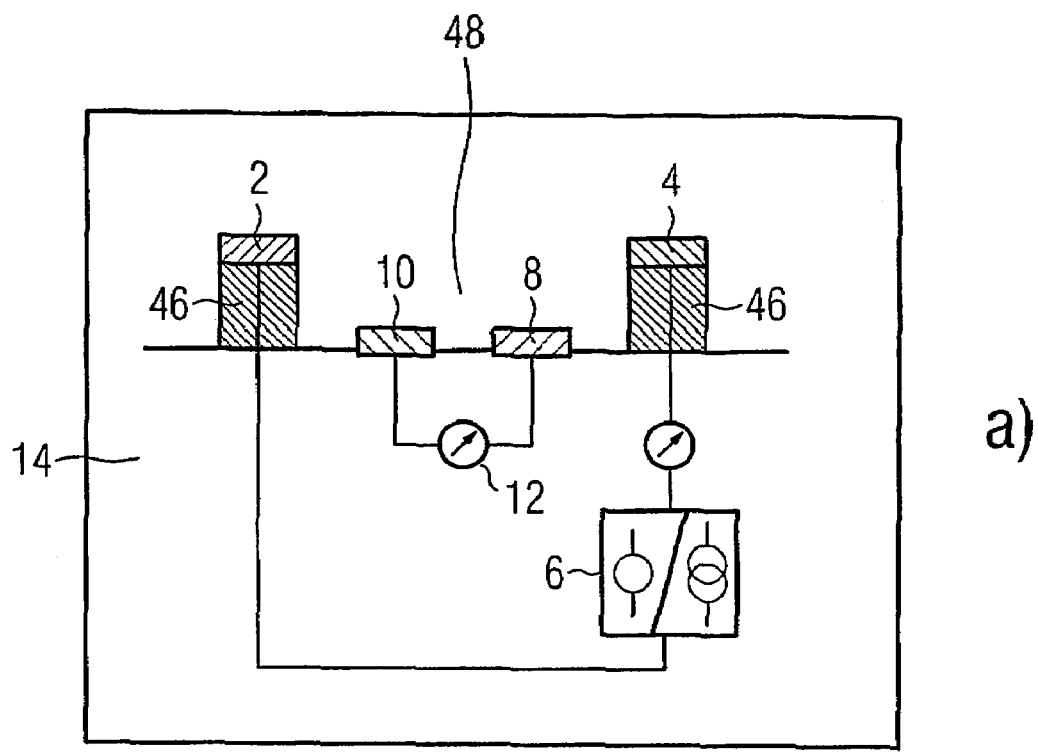
FIG. 5 shows the section through the electrode microsystem from FIG. 1 along the line IV-IV with electrodes that lie on ridges and are partly (a) and completely (b) buried.
Figure 5:
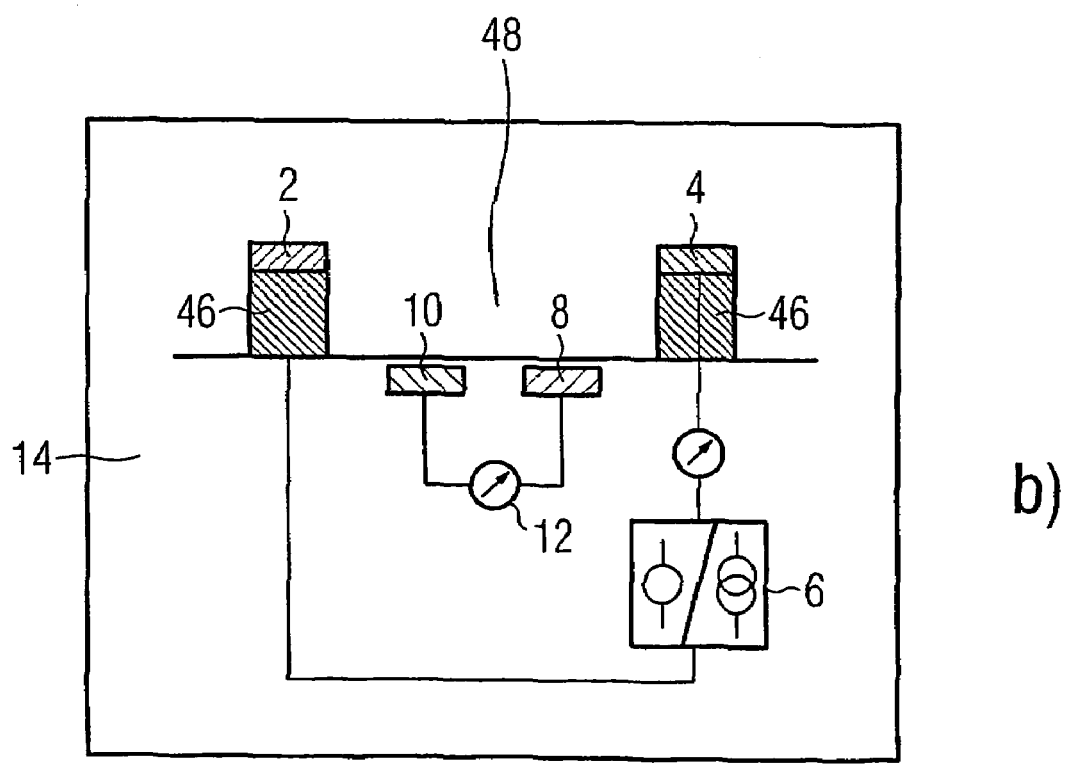

A section through FIG. 1 along the line IV-IV is illustrated in FIGS. 4 and 5. FIG. 4*a* illustrates the construction of the carrier 14 comprising the actual, generally monocrystalline, chip carrier, that is to say the substrate 34, e.g. silicon, and an electrically insulating layer 36, e.g. silicon oxide. The electrodes 2, 4, 8 and 10 are electrically insulated from one another by the insulating layer 36 and the interspaces 16. The analyte 38, which is in contact with the chip surface and the electrodes, is permeated by current lines 40 ending in the polarization electrodes 2 and 4. The current lines 40 arise as a result of the polarization current being fed in from the current source 6 into the analyte 38 by way of the polarization electrodes 2 and 4.

In the case of the latter arrangement, catcher molecules can be applied in a very thin layer 42 directly on the chip surface. Methods for this purpose are known sufficiently from the prior art. A target molecule from the analyte 38 can diffuse to the catcher molecule in the layer 42. It is only in the layer 42 that binding events can thus take place at all and can only be detected there. The detection takes place because in the layer 42 the electrical properties of the medium change on account of the binding events.

The current and voltage conditions in the analyte 38 change and a correspondingly changed voltage is tapped off at the sensor electrodes 8 and 10. As can be seen from the profile of the current lines 40, however, only a very small proportion of the field-permeated space is used for the reaction. The alterations of the electrical properties of the analyte that occur in an arrangement of this type and hence the detectable voltages between the sensor electrodes 8 and 10 may, if appropriate, lie below the metrologically detectable range of measurement voltages.

An improvement may occur by applying a reaction layer 44 to the DNA chip, as shown in FIG. 4*b*. In the reaction layer 44, for example a hydrogel, catcher molecules may be embedded or fixed in its entire volume. The reaction layer 44 is embodied with a thickness of only approximately 5-10 μm. Consequently, a chemical reaction can take place between target molecules from the analyte 38, which can diffuse rapidly into the very thin reaction layer 44, and the catcher molecules. The chemical reaction or alteration of electrical parameters in the reaction layer 44 is thus pervaded by a substantially larger range of current lines 40. Therefore, substantially larger voltages are measured at the voltmeter 12 during a reaction.

In FIGS. 5*a* and 5*b*, the polarization electrodes 2 and 4 lie on electrically insulating ridges 46 at a distance from the surface of the carrier 14. In specific cases, that is to say for specific combinations of immobilized species and analyte, this may lead to a more favorable field distribution in the analyte space 48. More favorable means that a largest possible voltage difference between the sensor electrodes 8 and 10 can be measured at the voltmeter 12.

In FIG. 5*a*, the two sensor electrodes 8 and 10 are partly buried in the carrier 14. In FIG. 5*b*, these two electrodes are completely buried and thus directly electrically isolated from the analyte space 48. The degree of burying or the direct electrical isolation may be more favorable or less favorable for obtaining reliable measurement results at the voltmeter 12, depending on analyte 38 and immobilized species. The selection of ridges 46 as carriers for the polarization electrodes 2 and 4 may also be more favorable or less favorable, depending on the situation. A corresponding selection of the structural arrangement can be found experimentally in most cases.

Figure 6A:
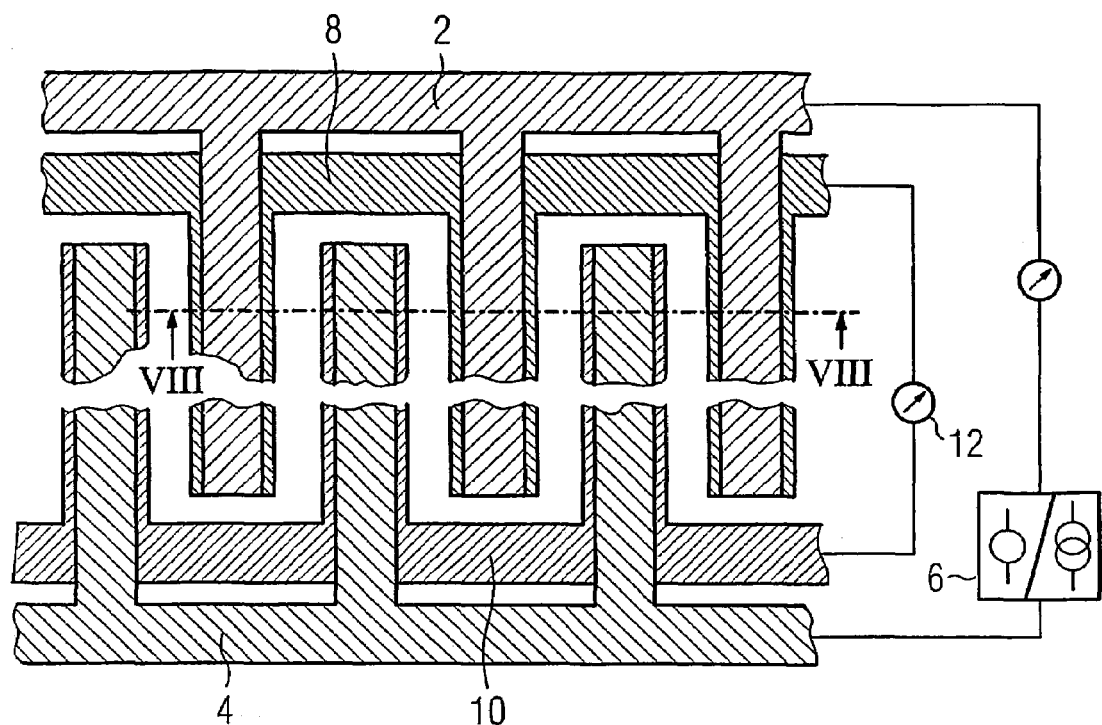
FIG. 6 shows electrode arrangements in plan view in an interdigital structure (a) and with buried electrode collective lines and plated-through holes (b)
Figure 6B:
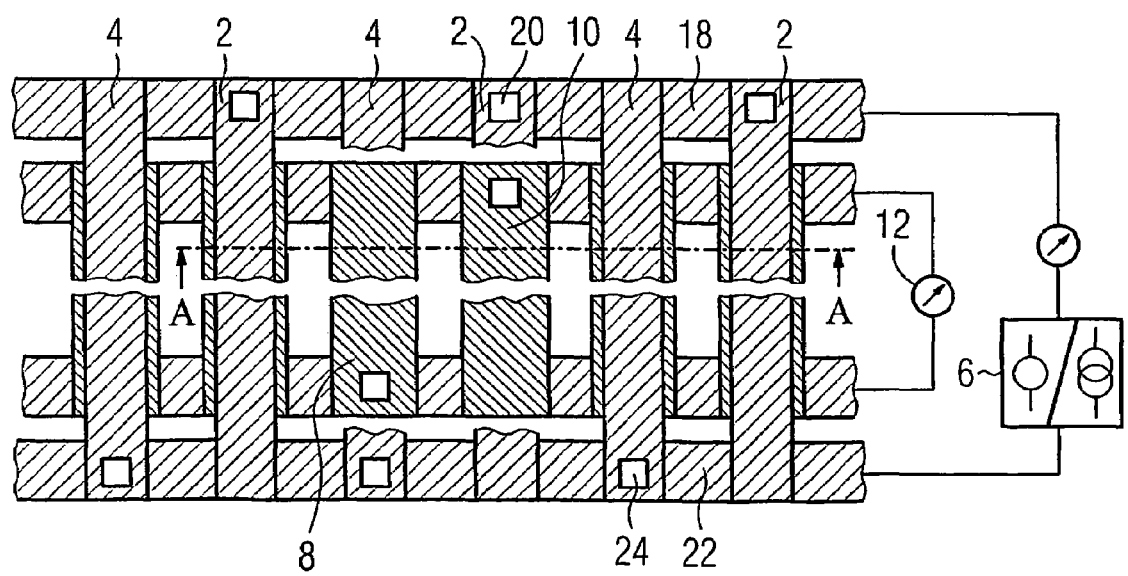

FIGS. 6*a* and 6*b* once again show different embodiments for the configuration and for the connection technique of the different electrodes with regard to the layout and the technologies used in the semiconductor process during chip fabrication. FIG. 6*a* corresponds to the embodiment in FIG. 1 with regard to the polarization electrodes 2 and 4. However, here the sensor electrodes 8 and 10 lie in approximately the same layout as the polarization electrodes 2 and 4, but below the latter, separated by an electrically insulating intermediate layer, that is to say ridges 46.

Figure 8:
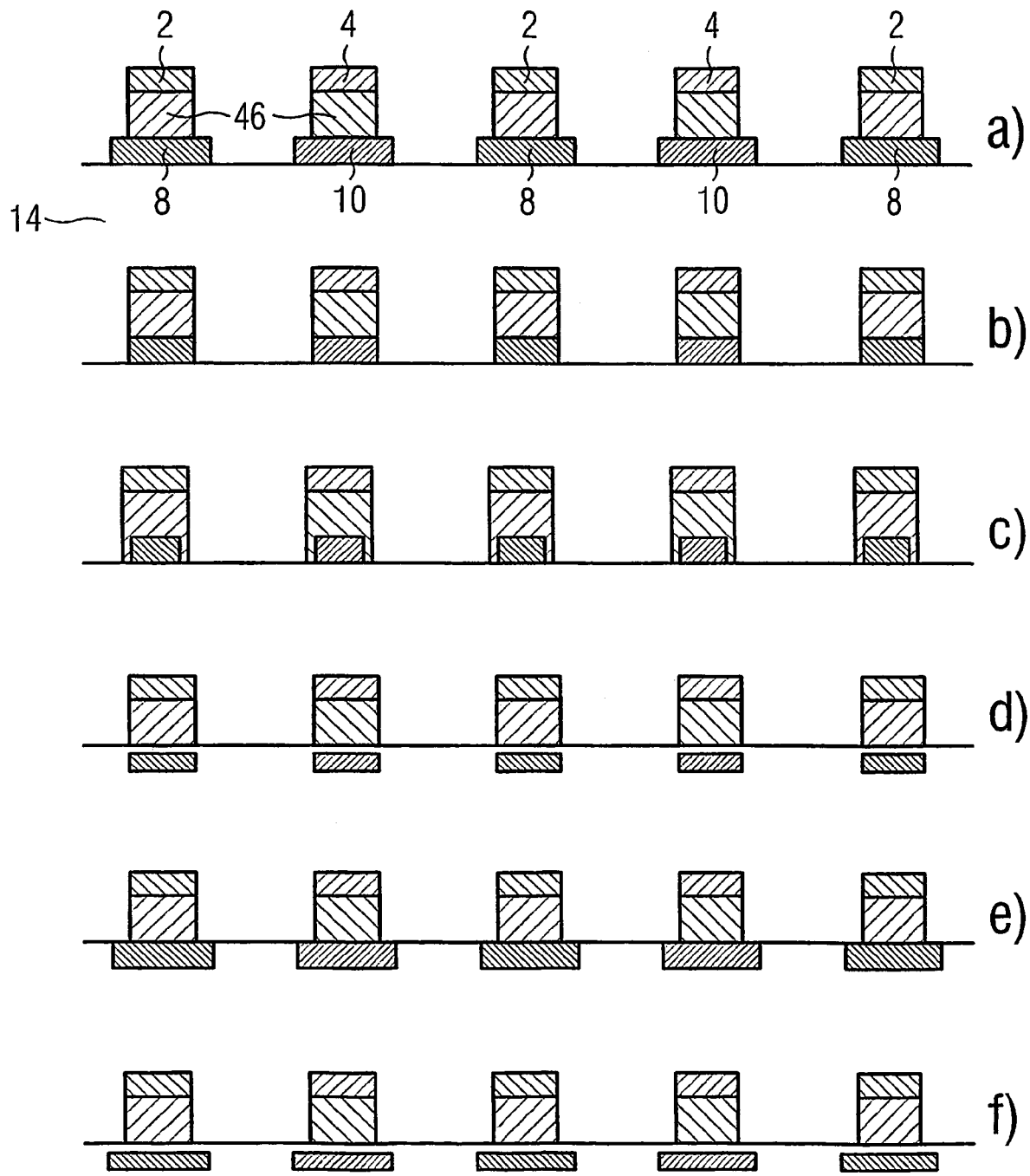
FIG. 8 shows electrode arrangements in cross section with polarization and sensor electrodes lying one above the other in different embodiments (a) to (f)

A section through this arrangement is illustrated in FIG. 8. Such a construction of the DNA chip achieves a very compact construction which permits virtually the smallest possible feature size and distances between one another that can be achieved in the semiconductor process for both types of electrode, that is to say sensor and polarization electrodes 4 and 2. Moreover, the construction of electrodes arranged one above the other influences the effective ratio between the size of both types of electrode in a similar manner to the configuration shown in FIG. 3, that is to say that the sensor electrodes 8 and 10 exhibit a small size in relation to the polarization electrodes 2 and 4.

FIG. 6b corresponds to the arrangement illustrated in FIG. 2, except that here, too, as in FIG. 6a, the electrode types are arranged one above the other instead of one beside the other. In the configuration illustrated in FIG. 6b, too, the polarization electrodes 2 and 4 again lie on the electrically insulating ridges 46 above the sensor electrodes 10 and 8, the ridges not being visible from the plan view.

A section along the line A-A through the arrangement as in FIG. 6a corresponds to FIG. 8 here, too, except that the electrodes lying one above the other are interchanged. Thus, the polarization electrodes 2 and 4 lie above the sensor electrodes 10 and 8, respectively.

The selection of the technologies or layouts used usually depends on the conditions or boundary conditions of the semiconductor process to be used and the object to be achieved with the DNA chip. Of course, it is also possible to use combination options from the techniques presented. Thus, it is conceivable, by way of example, to embody the polarization electrodes in accordance with FIG. 6a in a comb-like interdigital structure and to embody the sensor electrodes in accordance with FIG. 6b as individual strips through-connected to collective lines and to separate the two arrangements by means of ridges 46 and to arrange them one above the other.

Figure 7:
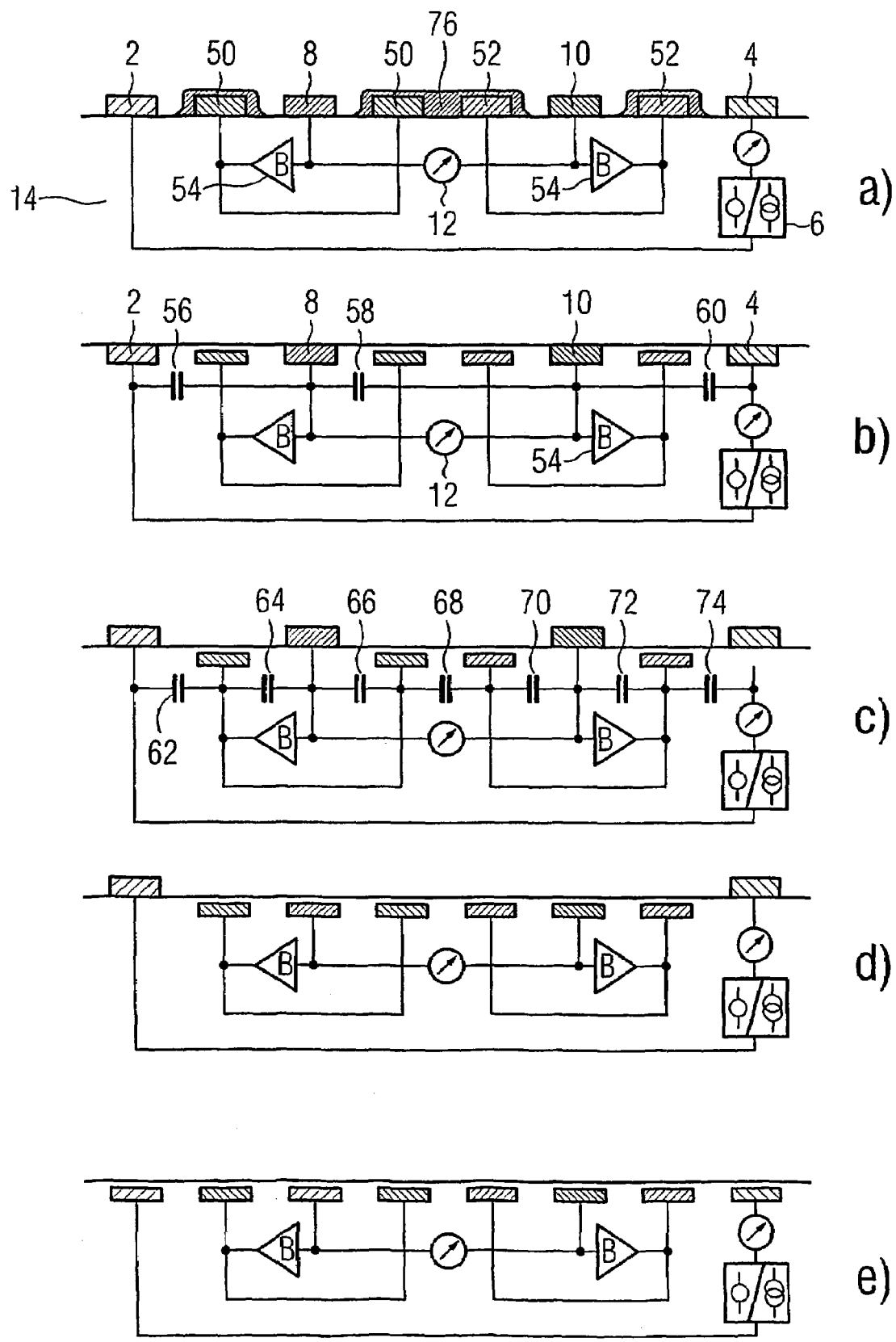
FIG. 7 shows electrode arrangements in cross section with shielding electrodes and differently insulated and buried electrodes (a) to (e)

In FIG. 7, each sensor electrode 8 and 10 is respectively assigned two shielding electrodes 50 and 52. By way of buffer amplifiers 54, the respective electrical potential of the sensor electrodes 8 and 10 is held in electrically active fashion at the shielding electrodes 50 and 52. The parasitic capacitances 56, 58 and 60—which are effective in the case of shielding electrodes being absent—between sensor electrodes 8 and 10 and polarization electrodes 2 and 4 become partly electrically ineffective by virtue of this measure, as is readily apparent from an electrical equivalent circuit diagram (not illustrated) of the arrangement. This is because the parasitic capacitances 62 to 74 form with shielding electrodes present.

However, only the capacitances 62, 68 and 74 of said parasitic capacitances are effective for the measurement in the measuring apparatuses of voltmeter 12 and the ammeter assigned to the current source 6. The other capacitances are supplied via the buffer amplifiers 54, that is to say are charged and discharged via the latter and, consequently, do not influence the measurement, which generally leads to a significantly improved measurement result. Consequently, these parasitic capacitances can no longer have a disadvantageous effect on the impedance between the sensor and polarization electrodes.

The buffer amplifiers 54 may be realized with the aid of semiconductor technology. This is directly in the carrier 14 beneath the electrode arrangement. This shortens signal paths, keeps additional capacitances as small as possible and, consequently, has a favorable influence on the frequency properties of the entire measuring arrangement. The various embodiments illustrated in FIG. 7 for arrangement of the individual electrodes differ by the fact that one or more electrodes are directly electrically isolated from the analyte or are completely or partially buried in the substrate.

The direct electrical isolation is effected, as in FIG. 7a, e.g. by oxidation of an additional oxide layer above the electrodes or by burying the electrodes, as carried out in FIG. 7e for all of the electrodes involved. In FIG. 7, too, different combinations between the alternatives illustrated are again conceivable. These may be adapted by way of simulations or experimentally to the requirements of a specific measurement or configuration of the chip.

FIG. 8 also illustrates a wide variety of combinations of the arrangement of sensor and polarization electrodes. While the polarization electrodes always rest on ridges above the carrier, the sensor electrodes are in each case arranged beneath or within the ridges. These measures make it possible to achieve an extremely compact design of the DNA chip since the spacings between the electrode types can be minimized.

Figure 9:
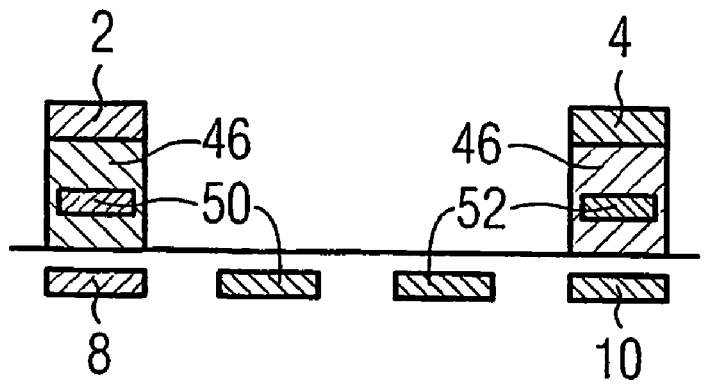
FIG. 9 shows electrode arrangements in cross section with examples of combinations of the various arrangement techniques (a) to (d), in each case in a basic illustration.
Figure 9:
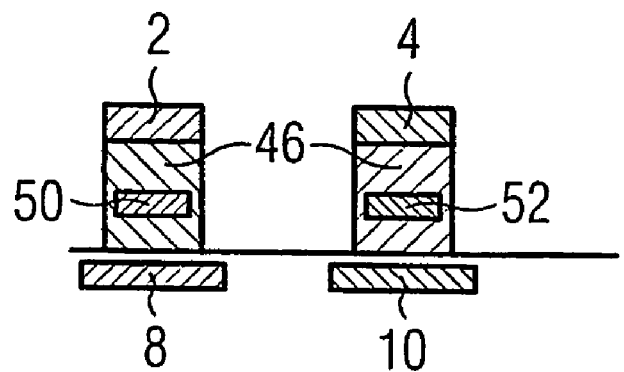
Figure 9:
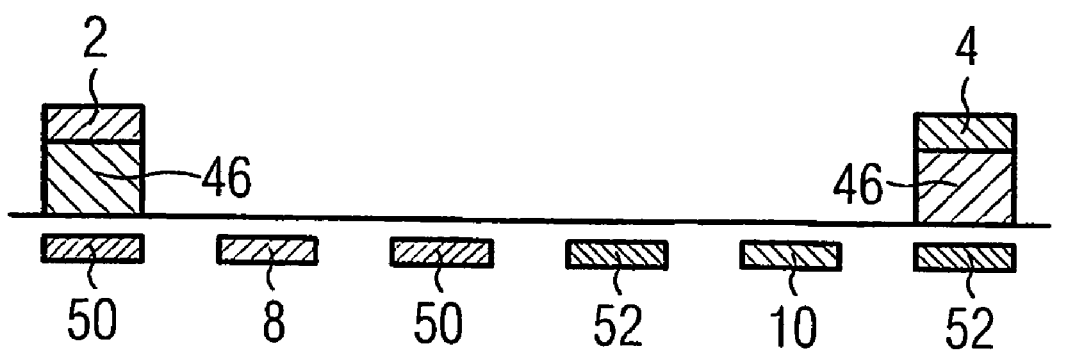
Figure 9:
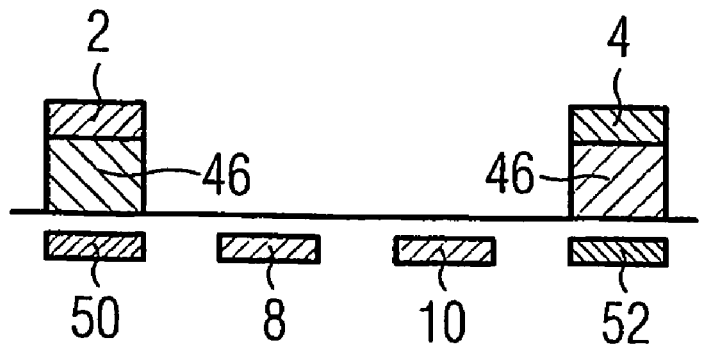

FIG. 9 shows configurations of electrodes corresponding to FIGS. 8, here one or more shielding electrodes additionally being provided between sensor electrodes among one another or between sensor and polarization electrodes. With regard to the selection of a specific configuration, the statements above also hold true for the arrangements illustrated in FIG. 9.

The embodiments illustrated in the figures are examples of the various combination options from the techniques presented. Of course, as mentioned a number of times, combinations other than those explicitly illustrated are also possible.

The present invention being thus described, it will be obvious that the same may be varied in many ways. Such variations are not to be regarded as a departure from the spirit and scope of the present invention, and all such modifications are intended to be included within the scope of the present invention.

The invention claimed is:

1. A DNA chip, comprising:
   a carrier; and
   a microarray of spots, arranged on the carrier, containing immobilized catcher molecules, each spot containing a thin-film four pole system for impedance-spectroscopic detection of binding events between the catcher molecules and target molecules of an analyte solution applied to the spots the thin-film four-pole system including two polarization electrodes for generating an alternating electromagnetic field and two sensor electrodes for measuring a voltage drop in the analyte.

2. The DNA chip as claimed in claim 1, wherein the carrier includes a silicon substrate on which the microelectrode system is integrated using thin-film technology.

3. The DNA chip as claimed in claim 1, wherein at least one sensor electrode is assigned a shielding electrode, which is held at the same electrical potential as the sensor electrode.

4. The DNA chip as claimed in claim 3, wherein the electrical potential of the sensor electrode is held at the shielding electrode by a buffer amplifier connected to the sensor electrode and having a gain of 1.

5. The DNA chip as claimed in claim 4, wherein the buffer amplifier is integrated on the carrier.

6. The DNA chip as claimed in claim 1, wherein at least one of at least one sensor electrode and at least one shielding electrode are directly electrically isolated from the analyte.

7. The DNA chip as claimed in claim 1, wherein a sensor electrode contains pointlike individual electrodes which are electrically connected to a buried electrode collective line by way of plated-through holes.

8. The DNA chip as claimed in claim 1, wherein the thin-film microelectrode system is embedded in a reaction layer containing catcher molecules.

9. The DNA chip as claimed in claim 8, wherein the thickness of the reaction layer is less than 100 μm and is correlated with the width of the electrodes or the interspaces thereof.

10. The DNA chip as claimed in claim 9, wherein the width of the electrodes is approximately 1 μm, and the thickness of the reaction layer corresponds to approximately 5-10 times the value of the electrode width.

11. The DNA chip as claimed in claim 8, wherein the reaction layer is a hydrogel.

12. The DNA chip as claimed in claim 1, wherein the thin-film four-pole system forms an interdigital current electrode arrangement with double meandering current taps.

13. The DNA chip as claimed in claim 2, wherein at least one sensor electrode is assigned a shielding electrode, which is held at the same electrical potential as the sensor electrode.

14. The DNA chip as claimed in claim 2, wherein at least one of at least one sensor electrode and at least one shielding electrode are directly electrically isolated from the analyte.

15. The DNA chip as claimed in claim 2, wherein a sensor electrode contains pointlike individual electrodes which are electrically connected to a buried electrode collective line by way of plated-through holes.

16. The DNA chip as claimed in claim 2, wherein the thin-film microelectrode system is embedded in a reaction layer containing catcher molecules.

17. The DNA chip as claimed in claim 9, wherein the reaction layer is a hydrogel.

18. The DNA chip as claimed in claim 2, wherein the thin-film four-pole system forms an interdigital current electrode arrangement with double meandering current taps.

* * * * *